(12) United States Patent
Roggenbuck

(10) Patent No.: US 8,058,019 B2
(45) Date of Patent: Nov. 15, 2011

(54) METHOD FOR ASSAYING ANTIBODIES IN BODY FLUIDS BY IMMUNE REACTION WITH GLYCOPROTEIN 2 (GP2) FROM ZYMOGENIC GRANULES OF THE PANCREAS FOR THE DIFFERENTIAL DIAGNOSIS OF INFLAMMATORY INTESTINAL DISEASES AND CHRONIC PANCREATITIS

(75) Inventor: Dirk Roggenbuck, Dahlewitz (DE)

(73) Assignee: GA Generic Assays GmbH (DE)

( * ) Notice: Subject to any disclaimer, the term of this patent is extended or adjusted under 35 U.S.C. 154(b) by 37 days.

(21) Appl. No.: 12/523,997

(22) PCT Filed: Jan. 28, 2008

(86) PCT No.: PCT/DE2008/000183
§ 371 (c)(1),
(2), (4) Date: Mar. 18, 2010

(87) PCT Pub. No.: WO2008/089756
PCT Pub. Date: Jul. 31, 2008

(65) Prior Publication Data
US 2010/0184662 A1 Jul. 22, 2010

(30) Foreign Application Priority Data

Jan. 26, 2007 (DE) .......................... 10 2007 004 909
Jan. 26, 2007 (EP) ...................................... 07090010

(51) Int. Cl.
*G01N 33/53* (2006.01)

(52) U.S. Cl. ...................................................... 435/7.2

(58) Field of Classification Search .................. None
See application file for complete search history.

(56) References Cited

U.S. PATENT DOCUMENTS 6,100,098 A 8/2000 Newkirk

FOREIGN PATENT DOCUMENTS

| JP | 2004 005319 A | 1/2004 |
|---|---|---|
| WO | 96/17873 A1 | 6/1996 |
| WO | 01/94409 A2 | 12/2001 |
| WO | 2006/022643 A1 | 3/2006 |

OTHER PUBLICATIONS

Bossuyt: "Serologic Markers in Inflammatory Bowel Disease" in Clinical Chemistry, vol. 52, No. 2, 2006, pp: 171-181.
Peeters et al: "Diagnostic Value of Anti-*Saccharomyces cerevisiae* and Antineutrophil Cytoplasmic Autoantibodies in Inflammatory Bowel Disease" in American Journal of Gastroenterology, New York, NY, vol. 96, No. 3, Mar. 1, 2001, pp. 730-734.
Fukuoka: "Molecular Cloning and Sequences of cDNAs Encoding Alpha (large) and Beta (small) Isoforms of Human Pancreatic Zymogen Granule Membrane-Associated Protein GP2" in Biochimica Et Biophysica Acta, Gene Structure and Expression, Elsevier, Amsterdam, NL, vol. 1491, No. 1-3, Apr. 25, 2000, pp. 376-380 & DATAbase UniProt XP002440349—Oct. 2006: Accession No. P55259 (abstract).
Wong et al: "Sequence of the cDNA Encoding Human GP-2, the Major Membrane Protein in the Secretory Granule of the Exoerine Pancreas" in Gene, Elsevier, Amsterdam, NL, vol. 171, No. 2, Jun. 1, 1996, pp. 311-312.

*Primary Examiner* — Michael Pak
(74) *Attorney, Agent, or Firm* — Joyce von Natzmer; Pequignot + Myers LLC

(57) ABSTRACT

The invention relates to a method for the detection of antibodies from body fluids via immune reaction with GP2 from pancreatic zymogenic granules, immunoreactive sequences or analogs thereof, excluding tissue sections.

16 Claims, No Drawings

METHOD FOR ASSAYING ANTIBODIES IN BODY FLUIDS BY IMMUNE REACTION WITH GLYCOPROTEIN 2 (GP2) FROM ZYMOGENIC GRANULES OF THE PANCREAS FOR THE DIFFERENTIAL DIAGNOSIS OF INFLAMMATORY INTESTINAL DISEASES AND CHRONIC PANCREATITIS

This is the U.S. national stage of International application PCT/DE2008/000183, filed Jan. 28, 2008 designating the United States, which claims priority from German Patent application DE 10 2007 004 909.0, filed Jan. 26, 2007 as well as from European Patent application EP 07090010.5, also filed Jan. 26, 2007.

The invention relates to a method for the detection of antibodies from body fluids via immune reaction with GP2 from pancreatic zymogenic granules, immunoreactive sequences or analogs thereof, excluding tissue sections.

The method can be used in the diagnosis or therapy control of diseases associated with an immune reaction to GP2 and analogous substances. More specifically, the invention is therefore directed to the use of GP2, immunoreactive sequences or analogs thereof in the diagnosis or therapy control of chronic inflammatory or autoimmune diseases, especially Crohn's disease (CD) and chronic pancreatitis (CP).

The present invention is based on the finding that GP2 is an autoantigen of immune processes in inflammatory bowel diseases (IBD), preferably in CD and CP, thus representing an epitope of disease-associated antibodies.

GP2 is a membrane glycoprotein of the acinar cells of the pancreas with an apparent molecular weight of 78 kDa. Furthermore, GP2 has been detected in the brush-border cells of the intestine and as a component of lysosomes or as free, non-membrane-bound peptide in pancreatic juice. Making up 30 to 45% of the overall membrane protein, it represents the main component of the zymogen granule membrane. Together with other secretory pancreatic proteins of the zymogenic granules, such as syncollin, lectin ZG16p, synaptobrevin 2 and other sulfate matrix proteoglycans, GP2 is a component of lipid rafts of the granular membrane, and syncollin interacts with GP2. These complexes, also including other proteins such as ZG46p, form the submembranous matrix.

GP2 is bound to the zymogen granule membrane of the pancreatic acinar cells via a phosphatidyl inositol anchor and can be removed e.g. by phospholipase C of *B. cereus*. Zymogenic granules are the reservoirs of digestive enzymes, such as amylase, in the acinar cells of the pancreas. Following neuronal or hormonal stimulation of the acinar cells, the digestive enzymes are secreted into the pancreatic ducts. GP2 is not only localized on the zymogen granule membrane but is also found in the matrix thereof, in the Golgi apparatus as well as in the lumen of the acini in pancreatic juice. Furthermore, it appears that GP2 is a component of lysosomes and therefore involved in endocytosis.

During stimulation of pancreatic secretion, GP2 is transported to the apical membrane surface of the acinar cells, cleaved off, and released into the acinar lumen. In view of the relatively large amount of GP2 in pancreatic juice, another cellular pool is suspected to exist, from which GP2 can be secreted. In contrast to digestive enzymes activated in the intestine via proteolysis, GP2 is already modified in the acinar cells by cleavage. It is assumed that the intracellular sequential proteolysis of GP2 has an influence on the function thereof.

The augmented serum levels of GP2 in acute and chronic pancreatitis have led to discussions relating to the suitability of GP2 as marker in serological diagnostics of such entities. In a rat model the serum concentration of GP2 has been demonstrated to correlate with the severity of inflammatory bowel diseases.

For human cell lines such a relationship has not been as yet established beyond any doubt; the levels of GP2 detectable via autoantibodies show considerable individual variability.

Despite this disadvantage, a number of approaches to developing diagnostic methods rely on the production and detection of antibodies directed against GP2 so as to determine the severity of inflammatory bowel diseases from the antibody reaction.

CD and ulcerative colitis (UC) represent the two most important among inflammatory bowel diseases. They are characterized by chronic, relapsing tissuedestroying inflammatory processes in the digestive system. To date, etiology and pathogenesis of CD as well as UC are unclear.

While inflammation in UC predominantly appears in the mucosa and submucosa of colon and rectum, CD is characterized by wall-penetrating, granulomatous inflammatory processes of the entire gastrointestinal tract.

Genetic as well as environmental factors seem to play a crucial role in the development of IBD. The connection between mutations in the NOD2 gene and the appearance of CD must be regarded as well-established in several cohorts. Similarly, there is a clear association regarding the appearance of CD in the terminal ileum. To date, a relationship between genetic markers and course of therapy has not been established in any treatment method (including the anti-TNF therapy).

The incidence of CD in Europe is around 5.6 per 100,000 per year. The prevalence of CD in Germany has been stated to be $\frac{1}{500}$ to $\frac{1}{800}$.

On an average, the first symptoms of CD appear relatively early at an age of 30 years. Consequently, CD patients are affected in their working life, with corresponding socio-economic effects. In a similar manner as in UC, the incidence of carcinoma is increased in CD patients with Crohn's colitis and a course lasting many years.

The clinical picture comprises abdominal pain, diarrhea, malabsorption, abscesses, fistula, gallstone complications, renal stones and complications associated therewith.

CD patients may exhibit a number of extraintestinal manifestations, with pancreatitis—amounting to 3.5%—being a relatively rare event in CD patients. However, hyperamylasemia and hyperlipasemia with no signs of acute pancreatitis can be observed in 8-17% of the patients, indicating an increased rate of silent pancreatitis. Changes in the pancreatic ducts and restrictions of the pancreatic function have been described in some cases. The level of hyperamylasemia and hyperlipasemia correlates with the activity of CD. In a similar manner as in patients with primary sclerosing cholangitis, simultaneous changes in the biliary and pancreas ducts are found in 4.6% of CD patients. However, chronic pancreatitis in CD patients is usually different from that in UC where involvement of the biliary ducts, weight loss and pancreatic duct stenoses are more frequently seen. There have been discussions on the existence of an idiopathic chronic pancreatitis associated with CD. In contrast to UC-associated chronic pancreatitis, the intestinal symptoms in CD patients frequently appear prior to pancreatic findings. Exocrine pancreatic insufficiency, which is frequent in CD, can easily be attributed to a marked acinar degeneration in association with dense inflammatory infiltrates in the parenchyma.

Administration of 5-aminosalicylic acid has been recommended as therapy, although various studies have pointed out considerable drawbacks because this active substance has achieved only limited or no effects at all. In view of the available data, however, use thereof in patients having mild to moderately severe attacks seems quite justified when timely initiating a change in therapy in the event of ineffectiveness. In the event of severe attacks without complications, administration of prednisolone equivalents should be considered. If attacks are frequent ($\geq$2/year), azathioprine or 6-mercaptopurine can be administered in addition.

In Germany, the overall costs of a CD patient are estimated to be 20,000 EUR per year and case. The costs for CD patients, including indirect expenses, are estimated to be 2 billion EUR in Germany, while 2.6 billion US dollars as socioeconomic costs are reported in the USA for both IBDs.

Anti-TNF$\alpha$ preparations are effective on CD, inducing remission of the chronic disease. However, these preparations are disadvantageous due to their side effects, which is why their use is possible only as reserve medications, depending on the clinical situation. It is only CD patients with an active spondyloarthropathy as extraintestinal complication who seem to benefit from an anti-TNF$\alpha$ therapy in both clinical pictures.

Clear diagnosing is necessary for adequate therapy and follow-up of these patients. However, this involves a considerable disadvantage because unambiguous tests are not available as yet so that clinical diagnosing of CD must be used which involves ileocoloscopic segmental biopsies as an essential component, the latter also being indicated prior to selective intestinal surgery. However, this is not invariably necessary in any acute symptomatic complex during the course thereof or prior to a new anti-inflammatory therapy. Upper endoscopic diagnosing should be performed in each patient during primary diagnostics.

Highly complex and comparatively cost-intensive histological investigations of mucosa biopsies constitute another important element within the scope of diagnostics. To this end, biopsies are collected especially from macroscopically conspicuous as well as inconspicuous areas. To efficiently utilize the potential of histopathological differential diagnostics it is, however, necessary to collect biopsies from at least five different anatomic segments of the entire colon, including the rectum, from the terminal ileum and upper gastrointestinal tract.

Transabdominal ultrasound as imaging method is used as a sensitive method of detecting inflammatory changes of the intestinal wall, as well as abscesses, fistulas and stenoses in CD patients. A detectable increase in bloodflow both in the mesenteric arteries and in the intestinal wall is associated with the presence of acute inflammation. Endorectal ultrasound and magnetic resonance tomography (MRT) of the minor pelvis have been recognized as equally sensitive methods in the diagnostics and classification of anorectal fistulas and abscesses.

Since no unambiguous tests are available, a number of parameters for laboratory diagnostics of CD are collected. The determination of C-reactive protein (CRP), thrombocytes, hemoglobin (Hb)/hematocrit and leukocytes represents the basic diagnostics. Other parameters such as differential blood count and albumin are used in addition. In the acute phase of CD the above-mentioned parameters such as CRP, the number of leukocytes as well as acute-phase proteins are increased in many patients and have also been recommended in follow-up.

During the acute phase there is an increase in intestinal permeability, alpha1-antitrypsin clearance and excretion of calprotectin in stool.

However, collection of clinical and histological data does not allow clear differentiation between CD and UC. This drawback frequently has resulted in the definition of an indeterminate colitis (IC). Furthermore, intestinal infections as well as functional diseases may develop similar symptoms and make differential diagnosis much more difficult. In 10 to 15% of IBD patients, classification into UC or CD is extremely difficult from the biopsy data and due to some overlap of clinical symptoms in the region of the colon. Following surgical intervention, patients with IC seem to have long-term complications and anastomotic insufficiency more frequently than patients with UC. However, a differentiation whether IC patients, in prognostic terms, will develop in the direction of CD or UC has a substantial influence on the prognosis and course of the disease and on selecting a drug-based therapy and the time of surgical intervention. At a later point in time during the course of the disease, an assignment is frequently only possible on the basis of additional clinical data. For example, differentiation between CD and UC is the basis when making a decision whether ileoanal pouch anastomosis could be envisaged in a patient. Such surgical intervention is rarely indicated in CD patients with predominant affection of the colon (Crohn's colitis), while this method is more frequently indicated in the event of UC. CD patients have a significantly higher rate of anastomotic insufficiency so that any surgical intervention requires thorough consideration.

A number of antibodies reacting with endogenic and food antigens have been described in the context with differential diagnosis of IBD. These antibodies, however do not seem to play any pathogenetic role and fail to reflect the activity of the disease. Nevertheless, serological antibody diagnostics is utilized as a crucial aid in diagnosing and represents the basis of therapeutic decisions particularly in the event of indeterminate colitis.

Autoantibodies against cytoskeletal proteins have been described in CD patients confirmed by means of biopsy (Mayet et al., 1990). Autoantibodies against cytokeratin 18, actin, vimentin, desmin and tropomyosin have been found among others. Although cytokeratin 18 autoantibodies have been found to correlate with the activity of the disease, they failed to gain acceptance in IBD routine diagnostics, probably as a result of their low specificity.

For CD patients, autoantibodies against tissue of exocrine pancreas (PAK) and antibodies against mannan from *Saccharomyces cerevisiae* (ASCA) have been identified as being pathognomonic (Stacker et al., 1987; Main et al., 1988). Autoantibodies against human neutrophilic granulocytes (ANCA) and goblet cells (BAK) are mainly found in UC patients.

The determination of PAK, ANCA and ASCA is regarded as useful in diagnosing IC.

However, even today, due to the unknown autoantigens responsible for immune reaction, IBD-specific autoantibodies against pancreatic tissue, goblet cells and human neutrophilic granulocytes are still determined using immunofluorescence technology (IFT). Thus, using the above technology, autoantibodies against pancreatic antigens have been found in 27 to 39% of CD patients. More than half of the CD patients (68%) with extraintestinal complications may have PAK. In practice, however, this technology has been found to be disadvantageous because it cannot be automated and is therefore cost-intensive and time-consuming.

In contrast, ASCA being likewise specific for CD are detected at increased levels in an enzyme immunoassay (EIA) because this method is less subjective in terms of evaluation and can be automated.

Today, separate antibody determinations are regarded as too insensitive for serological diagnostics of CD. Combining different antibody specificities can highly improve the diagnostic sensitivity or specificity in differential diagnosis of IBD and allow a prognosis in IC.

A common technological platform such as EIA is extraordinarily advantageous in combining parameters. One precondition, however, is to know the PAK autoanti-gen which is specifically recognized by the PAK in pancreatic tissue sections of different species.

The past has seen various approaches to identify the autoantigens in CD, and the focus of interest has been on pancreatic antigens because of the above-mentioned relatively high sensitivity of PAK. Using tissue sections of various species (human, rat, monkey), PAK have been detected by means of IFT. Regarding the phylogeny, this suggests conserved epitopes recognized by PAK. Fricke et al. have described a protein complex consisting of a plurality of subunits with a molecular weight (m.w.) of more than 800 kDa, which react with PAK (Fricke et al., 1999). However, the authors have neither been able to sequence and thus identify the corresponding protein nor the subunits with m.w. 16, 18, 19, 24, 27, 29, 31 and 34 kDa reactive with PAK in the immunoblot. It has been assumed that the protein recognized by PAK should be a large protein complex including a number of subgroups. Based on inhibition experiments using various glycoproteins, reactivity of PAK with carbohydrate chains of putative autoanti-gens has been ruled out.

Seibold et al. have described the reactivity of PAK to a macromolecular antigen purified from pancreatic juice, with a m.w. of more than $10^6$ Da (1,000 kDa), which lost its PAK reactivity upon treatment with trypsin. No reactivity with PAK has been determined in ELISA with various pancreatic proteins such as amylase, lipase, phospholipase A and C, enterokinase, carboxypeptidase A and B, chymotrypsin A and B, chymotrypsinogen, elastase, trypsin, trypsin inhibitor, lactoferrin and callecrein.

Although, according to a number of authors, the level of GP2 and the severity of IBD correlate, the physiological context is unknown. As has been demonstrated in a knock-out mouse model, the absence of GP2 is neither essential to the secretion of the exocrine pancreas nor to the formation of zymogenic granules. Furthermore, the physiological function of the two known isoforms of GP2 is unclear (Fukuoca, 2000). In addition to a short isoform having a length of 380 amino acids, β-GP2, there is an α-GP2 530 amino acids in length. Both isoforms of the peptide can be detected in the tissue of human pancreas, among others, the small β-GP2 isoform occurring with substantially higher titers than the large α-GP2. Also, detection of the transcripts of both forms in pancreatic tissue shows stronger expression of β-GP2 compared to α-GP2.

The role of the different isoforms is unclear. Peptides having sequences highly similar to the large α-GP2 isoform are said to be responsible for pancreatic tumor formation. Antibodies to GP2 as analyte and marker are intended for use in diagnosing pancreatic cancer and the peptide and its nucleic acid sequence for use in immune therapy of cancerous diseases of the pancreas (WO 01/94409). Antibodies to the small β-GP2 isoform find use as markers of pancreatitis (WO 96/17873). An increase in β-GP2 concentration is said to be indicative of the disease.

Explicit reference has been made to the necessary—still to be found—identification of the pancreatic autoantigen(s) in order to clarify the status of autoimmune processes in the pathogenesis of CD and support discrimination of unclear IBD cases by appropriate laboratory diagnostics.

Attempts are known from the prior art wherein peptides have been obtained using randomized phage display libraries, which peptides have been employed in the determination of CD-specific antibodies. Four different nonamers were determined which gave positive detection in 56.5% of the serums of CD patients when used in an EIA. Control groups (UC, duodenal ulcer, healthy) gave no response or only in 6% of the cases. However, conclusions as to the native CD autoantigen(s) were not possible from the known peptide sequences of the nonamers.

To date, however, no success has been made in identifying the corresponding pancreatic antigen(s) (Bossuyt, 2006). Thus, a non-invasive, specific, quantitative, rapidly, easily and inexpensively feasible detection assay for diagnosing Crohn's disease and chronic pancreatitis and discriminating the latter from ulcerative colitis is not available as yet.

This problem is solved by the invention. Based on the surprising characterization of GP2 as autoantigen for CD and the associated chronic pancreatitis, a method in accordance with the claims was developed for the diagnosis or therapy control of IBD using GP2; advantageous embodiments of the invention can be inferred from the subclaims.

Accordingly, the invention relates to a method for the detection of antibodies from stool and/or body fluids, especially blood and/or serum, via immune reaction with GP2, immunoreactive sequences or analogs thereof, particularly according to SEQ ID NO 1:

```
         10         20         30         40         50         60
  MVGSGLLWLA LVSCILTQAS AVQRGYGNPI EASSYGLDLD CGAPGTPEAH VCFDPCQNYT 70         80         90        100        110        120
  LLDEPFRSTE NSAGSQGCDK NMSGWYRFVG EGGVRMSETC VQVHRCQTDA PMWLNGTHPA 130        140        150        160        170        180
  LGDGITNHTA CAHWSGNCCF WKTEVLVKAC PGGYHVYRLE GTPWCNLRYC TDPSTVEDKC 190        200        210        220        230        240
  EKACRPEEEC LALNSTWGCF CRQDLNSSDV HSLQPQLDCG PREIKVKVDK CLLGGLGLGE 250        260        270        280        290        300
  EVIAYLRDPN CSSILQTEER NWVSVTSPVQ ASACRNILER NQTHAIYKNT LSLVNDFIIR 310        320        330        340        350        360
  DTILNINFQC AYPLDMKVSL QAALQPIVSS LNVSVDGNGE FIVRMALFQD QNYTNPYEGD
```

```
             370        380        390        400        410        420
        AVELSVESVL YVGAILEQGD TSRFNLVLRN CYATPTEDKA DLVKYFIIRN SCSNQRDSTI 430        440        450        460        470        480
        HVEENGQSSE SRFSVQMFMF AGHYDLVFLH CEIHLCDSLN EQCQPSCSRS QVRSEVPAID 490        500        510        520
        LARVLDLGPI TRRGAQSPGV MNGTPSTAGF LVAWPMVLLT VLLAWLF
``` in the prophylaxis, diagnosis, therapy or aftercare of autoimmune diseases. According to the invention, the definition of body fluids also comprises human blood, serum, urine, pure pancreatic juices or duodenal juices.

The determination of autoantibodies to GP2 or use thereof in an ELISA as a solid-phase antigen in serological diagnostics of CD or chronic pancreatitis has neither been considered nor mentioned in the prior art.

The invention is directed to the surprising teaching that GP2, particularly according to the sequence SEQ ID NO 1, or the nucleic acid encoding the same can be used in the detection and treatment of autoimmune diseases, especially inflammatory bowel diseases, and more preferably Crohn's disease, chronic pancreatitis and ulcerative colitis.

In another aspect, the invention relates to a method wherein human IgA, IgM and/or IgG antibody autoimmune diseases are detected.

In a preferred embodiment of the method according to the invention the GP2 is of human, animal, recombinant or synthetic origin. GP2 represents a highly conserved peptide so that GP2 of any origin can advantageously be used for detection as long as the sequence is functionally analog to the sequence according to the invention. High binding affinity between the GP2 as antigen and the autoantibodies is retained.

In another preferred embodiment of the method according to the invention the autoantibodies are detected in an immunoassay, preferably with direct or indirect coupling of one reactant to a labelling substance. This enables flexible adaptation of the method to the potentials and requirements of different laboratories and their laboratory diagnostic equipment.

In one advantageous embodiment the IBD-specific antibodies are detected in an immunoassay wherein the antibodies are present dissolved in a liquid phase, preferably diluted in a conventional buffer solution well-known to those skilled in the art or in an undiluted body fluid. According to the invention, detection can also be effected using stool samples.

In another advantageous embodiment the immunoassay is used in the detection of antibodies, to which end binding of the GP2 antigen in accordance with SEQ ID NO 1 to a solid phase is envisaged. Following addition of sample solution, the patient's antibody included therein binds to the GP2 antigen. The antibody which is obtained e.g. from the serum or stool of a patient and bound to GP2 is subsequently detected using a labelled reagent and optionally quantified. This method wherein the antigen is bound to the solid phase is known as "direct assay" to those skilled in the art.

Thus, according to the invention, detection of the antibodies in this method is effected using labelled reagents according to the well-known ELISA (EnzymeLinked Immunosorbent Assay) technology. Labels according to the invention therefore comprise enzymes catalyzing a chemical reaction which can be determined by optical means, especially by means of chromogenic substrates, chemiluminescent methods or fluorescent dyes.

In another preferred embodiment the autoantibodies are detected by labelling with weakly radioactive substances in radioimmunoassays (RIA) wherein the resulting radioactivity is measured.

In another preferred embodiment of the invention, soluble or solid phase-bound GP2 molecules are used to bind the antibodies. In a second reaction step, anti-human immunoglobulins are employed preferably selected from the group comprising anti-human IgA, anti-human IgM and/or anti-human IgG antibodies, said anti-human immunoglobulins being detectably labelled conjugates of two components which can be conjugated with any conventional labelling enzymes, especially chromogenic and/or chemiluminescent substrates, preferably with horseradish peroxidase, alkaline phosphatase. The advantage of this embodiment lies in the use of ELISA technology usually available in laboratory facilities so that detection according to the invention can be established in a cost-effective manner.

In another preferred embodiment of the invention the antibody bound to GP2 reacts with anti-human immunoglobulins, preferably selected from the group comprising anti-human IgA, anti-human IgM and/or anti-human IgG antibodies, detectably coupled to fluorescein isothiocyanate (FITC). Much like the above-mentioned ELISA, the FITC technology represents a system that is available in many places and therefore allows smooth and low-cost establishment of the inventive detection in laboratory routine.

The invention also relates to a method for the treatment of inflammatory bowel diseases, comprising the following steps:
a) providing a column having GP2 coupled thereto;
b) passing the plasma of a patient over the column under conditions allowing effective binding of GP2 to antibodies in the patient's plasma, thereby removing a significant amount of antibodies from the plasma of the patient; and
c) returning the plasma thus obtained into the patient.

In a preferred embodiment of the above-mentioned method according to the invention, GP2 in accordance with SEQ ID NO 1 recognizes autoantibodies directed against intestinal tissue. This embodiment has the advantageous effect that diagnosis of IBD can simply be effected from body fluids or stool without interventions frequently involving stress to the patient.

In another preferred embodiment of the invention the GP2 in accordance with SEQ ID NO 1 is bound to a solid phase. Binding of GP2 in accordance with SEQ ID NO 1 to the solid phase can be effected via a spacer. All those chemical compounds having suitable structural and functional preconditions for spacer function can be used as spacers as long as they do not modify the binding behavior in such a way that binding of the GP2 autoantibody in accordance with SEQ ID NO 1 is adversely affected.

The inventive methods and uses allow diagnosis or therapy control of Crohn's disease because the GP2 antigen, preferably in accordance with SEQ ID NO 1, surprisingly allows detection of autoantibodies from stool and/or body fluids, especially blood and/or serum, via immune reaction with GP2, immunoreactive sequences or analogs thereof, said immune reaction being carried out without using tissue sections of animal or human tissue.

In a preferred variant of the above-described detection method the autoantibody is preferably detected using direct or indirect coupling of a reactant with a labelling substance.

According to the invention one may perform the above-described detection method on a solid phase, in which case the storability of the peptide is advantageously increased as a result of the surprisingly stable linkage of the GP2 anti-gen to the solid phase.

The invention is also directed to the use of the GP2 molecule in accordance with sequence SEQ ID NO 1 in the production of a medicament for use in prophylaxis, diagnosis, therapy and/or aftercare of autoimmune diseases. In practice, the use according to the invention has the advantageous effect that more complex and unreliable procedures based on e.g. biopsies, laboratory diagnostics and clinical interventions are dispensable in many cases, or that such measures—owing to the above-described detection—can be significantly optimized in their implementation.

In a preferred embodiment of the method the autoimmune disease is selected from the group of inflammatory bowel diseases (IBD) and/or autoimmune hepatic diseases, detection of which advantageously can be performed in a specific, reproducible and cost-effective manner, using the GP2 autoantigen.

In another preferred embodiment of the invention the inflammatory bowel disease is Crohn's disease, chronic pancreatitis and/or ulcerative colitis. To date, detection or differentiation of the above diseases was only possible with limited success or great efforts. The above preferred embodiment now enables easy detection of Crohn's disease and chronic pancreatitis and even differentiation from ulcerative colitis by means of differential diagnostics.

Crohn's disease belongs to the group of chronic inflammatory bowel diseases. It is a presumably autoaggressive, chronic-granulomatous inflammation which may appear in the entire gastrointestinal tract, i.e. from the oral cavity down to the anus. Affection is mainly in the lower small intestine (terminal ileum, affection about 40%) and colon, more rarely in esophagus and mouth. Crohn's disease is characterized by a discontinuous, segmental affection (so-called "skip lesions") of the intestinal mucosa, i.e., the disease can be present simultaneously in a plurality of intestinal sections separated by healthy sections. Other designations of the disease are regional enteritis, terminal ileitis, regional enterocolitis and sclerosing chronic enteritis, or the abbreviation CD (Crohn's disease), and IBD (inflammatory bowel disease) as a generic term. Accordingly, Crohn's disease in the meaning of the invention is any condition which is macroscopically characterized by the following changes:

Garden hose phenomenon: segmental stenoses caused by fibrosing

Cobble stone phenomenon: inflamed mucosa in alternation with deep ulcerations, thereby producing a cobble stone-like appearance Inflammatory conglomerate tumor: various intestinal sections adhere to each other.

Histologically, it is mainly accumulation of lymphocytes (eosinophilic), granulocytes and histiocytes that is recognized in the biopsies of inflamed intestinal tissue. Adjoining lymphatic nodes are usually increased in size. Frequently, there is formation of granulomas which can be differentiated into two types: epithelioid cell granulomas and microgranulomas (smaller and without central necrosis).

However, Crohn's disease in the meaning of the invention can also be characterized by way of diagnosis. In this event, Crohn's disease in the meaning of the invention is a condition where at least one of the following features can be detected:

Appendicitis: usually rapidly developing pain in the right lower abdomen.

Frequently, temperature difference >1° C. between rectal and axillary measurement.

Diverticulitis: palpable resistance, pain in lower abdomen usually on left side.

Yersiniosis: detection of pathogen from stool or biopsy material, increase in antibody titer.

Intestinal tuberculosis: very rare in Central Europe today. Intestinal tuberculosis is frequently accompanied by involvement of the lungs. "Cheesy" epithelioid cell granulomas are found in the biopsy material.

Any other invasive infectious colitis (*salmonella* enteritis, pseudomembranous colitis etc.)

Pancreatitis in the meaning of the invention is inflammation of the pancreas which can be acute or take a chronic course.

Pancreatitis is usually induced by activation of pancreatic enzymes within the organ. The function of these enzymes is to digest proteins and fat so that autodigestion of the organ is induced. Autodigestion results in inflammation of the pancreas. In severe cases, hemorrhage, serious tissue damage, infections and cysts may develop. An inflamed gland may cause enzymes to enter the bloodstream, thus reaching the lungs, heart and kidneys where further damage may arise. Acute pancreatitis develops when the pancreas suddenly becomes inflamed but recovers afterwards. Some patients suffer from acute pancreatitis a number of times but recover completely each time. Acute pancreatitis appears suddenly and can be a serious, life-threatening disease causing a large number of complications, but the patients normally recover from acute pancreatitis. The incidence is about five to ten new diseases per 100,000 inhabitants per year.

There are two types of courses:
1. Edematous pancreatitis: bland course with swelling of the organ and minor necroses in surrounding fatty tissue.
2. Hemorrhagic-necrotizing pancreatitis: extensive necroses and hemorrhages in the pancreas and into the neighboring area; often referred to as pancreatic apoplexy as a result of its fulminant symptoms.

Morphologic assessment of the pancreas, especially differentiation between edematous and necrotizing pancreatitis, is most successful when using contrast medium-enhanced computer tomography. The Balthazar score (0 to 10 points) was found useful in severity classification.

Acute pancreatitis may have several causes. The most frequent are gallstones which become stuck temporarily or for a prolonged period of time in the orifice of the biliary duct leading into the duodenum, which is also the orifice of the pancreatic duct (about 45% of acute pancreatitides). A similarly frequent cause is chronic alcohol abuse (about 35%). No distinct trigger factor can be determined in about 15% of affected individuals, and these cases are referred to as idiopathic genesis. In addition, there are rarer causes such as:

Side effects of drugs (e.g. asparaginase, azathioprin, furosemide, glucocorticoids, antibiotics (tetracyclines, sulfamethoxazole, trimethoprim), anticonvulsive agents (valproate, carbamazepine), propofol etc.

Infections, e.g. mumps, Coxsackie virus, hepatitis, HIV, cytomegaly virus

Elevated blood calcium values, e.g. in hyperparathyroidism

Strongly elevated blood fat (triglycerides)

Iatrogenic upon ERCP

Genetic: cystic fibrosis

Initially, acute pancreatitis becomes apparent by a pain in the (left to entire) upper abdomen (epigastrium) which radiates into the thorax and disappears after a few days. The pain is often vigorous and sometimes prolonged as well. The pain can be sudden and intense, or begin in the form of a mild pain which becomes worse upon ingestion of food (as a result of pancreas stimulation during form ation of pancreatic enzymes to digest the food). The abdomen can be swollen and highly sensitive. Abdomen painful to touch and a so-called rubber abdomen caused by meteorism and (moderate) guarding are characteristic in physical examinations. Likewise, there can be pain in the lower area of the thoracic spine. Initially, such pain is similar to a mild lumbago but subsequently develops more and more into a feeling of "being pierced" from the back to the region of the head of the pancreas on the abdominal side.

Patients with acute pancreatitis normally look very ill and actually have the feeling of being ill. Other symptoms are, for example, nausea, vomiting, obstipation, fever, accelerated pulse. In severe cases, jaundice (icterus) (in the event of obstructed biliary ducts), abdominal dropsy (ascites) (in the event of obstructed portal system), pleural effusion, shock and signs of sepsis appear in addition.

In laboratory diagnostics, an increased leukocyte count (leukocytosis) and an increase in the concentration of pancreatic enzymes (e.g. trypsin, amylases, lipase) are detected. Also, the calcium, magnesium, sodium, potassium, bicarbonate, sugar or fat values in blood can be increased.

About 20% of acute pancreatitis cases are serious. A patient could dehydrate and develop low blood pressure. Sometimes there are cardiac, pulmonary or renal failures. Acute pancreatitis in the worst cases results in hemorrhage, shock and sometimes death.

According to the current Atlanta classification, a differentiation between mild and severe acute pancreatitis is made.

An obsolete classification divides into an edematous form (early stage), a hemorrhagic form with local or generalized hemorrhages and an acute necrotizing form.

Chronic pancreatitis has many causes, but 70 to 80% can be attributed to chronic alcohol abuse. It appears more frequently in males than females and often develops between the age of 30 and 40. Chronic pancreatitis can also develop from an acute inflammation if the source is not eliminated or if the efferent duct is damaged.

Some of the chronic pancreatitides have hereditary causes. They are based on an abnormality of enzymes that are formed by the pancreas and cause tissue damages. Other forms of the disease are caused by external factors such as tobacco smoking.

During early stages of a pancreatitis a physician is often unable to decide whether an acute or chronic form is concerned. The symptoms may be the same.

Chronic pancreatitis frequently causes chronic pain. In some cases of chronic pancreatitis the pain abates as the disease progresses. It also gives rise to a pancreatic hypofunction, resulting in weight loss and disturbed digestion. Insufficient digestion and absorption lead to excretion of fats and proteins via the stool. Diabetes may develop if the endocrine cells (Langerhans islets) in the pancreas are damaged.

Diagnosing chronic pancreatitis is difficult; however, some highly advanced medical technologies are available. Pancreatic function blood tests may aid in deciding whether the pancreas is still capable of producing sufficient digestive enzymes. However, they barely found acceptance in practice. Abnormalities of the pancreas can also be recognized using sonography, ERCP and computer tomography.

During more advanced stages of chronic pancreatitis, wherein diabetes and malabsorption are seen, a physician may also perform blood, urine and stool tests for diagnosis.

Treatment of chronic pancreatitis involves prescription of analgesics and a change in diet. Patients can reduce the loss of fats and proteins by taking drugs containing pancreatic enzymes. The consequence of this will be improved nutrition and weight increase. Insulin or other medications are sometimes prescribed in order to control the blood sugar level.

In some cases of chronic pancreatitis, surgery is performed to alleviate pain by taking the strain from an enlarged and congested pancreatic duct.

In another preferred embodiment of the invention, GP2 is used to detect hepatic diseases, primary sclerosing cholangitis and/or autoimmune enteritides. Most surprisingly, the GP2 autoantigen is suitable not only for specific detection of IBD, but also for the detection of various hepatic diseases.

Cholangitis in the meaning of the invention refers to inflammation of the intrahepatic biliary ducts. It can be induced by various causes, including—among other things— obstruction of the biliary ducts by gallstones, stenoses, tumors or parasite infestation. It is differentiated into acute purulent cholangitis, non-purulent destructive cholangitis and chronic sclerosing cholangitis.

Acute purulent cholangitis: The acute cholangitis usually develops by infection during colonization with bacteria, mainly *Escherichia coli, Enterococcus* or *Klebsiella* species. Unilateral pain in the upper abdomen, fever and shaking chills appear as symptoms. Furthermore, severe purulent cholangitis gives rise to shock conditions, disorders of the central nervous system and renal dysfunctions. Treatment involves endoscopic intervention in the biliary ducts, such as endoscopic retrograde cholangiopancreatography (ERCP) or percutaneous transhepatic cholangiodrainage (PTCD), which restore the biliary flow, and usually antibiosis.

Non-purulent destructive cholangitis: This form of cholangitis takes a chronic course and is also referred to as primary biliary cirrhosis. 95% of affected individuals are females, and the incidence peak is between the age of 40 and 60. In diagnostic terms, antimitochondrial antibodies (AMA) are found in the blood of most patients so that an autoimmunological genesis is assumed. Clinically, the patients are characterized by itching, icterus and hypercholesterolemia. During the further course, help to a patient is only possible by means of liver transplantation.

Chronic sclerosing cholangitis: Chronic sclerosing cholangitis is the rarest biliary duct inflammation and is divided into a primary and a secondary sclerosing form. The primary form develops through infections in the presence of a pre-existing genetic disposition (an association with the HLA-B8 antigen has been determined) and affects males twice as often as females. p-ANCA is found in up to 90% of the cases. The secondary form develops on the basis of pre-existing immunodeficiency syndromes. As in destructive cholangitis, liver transplantation is necessary in the final stage.

Autoimmune enteritides in the meaning of the invention involve any form of enteritis, especially those being caused by chronic inflammatory bowel diseases. Also, autoimmune enteritides in the meaning of the invention involve those being caused by *salmonella, E. coli*, cholera or typhus pathogens, or by fungi, protozoa, toxic substances, but also any allergy-based enteritis or any form of actinic enteritis, *Yersinia* enteritis or bacterial dysentery.

In another preferred embodiment of the invention the amino acid sequence of the GP2 peptide has at least 60%, preferably 70%, more preferably 80%, especially preferably 90% homology to the sequence in accordance with SEQ ID NO 1. That is, the invention relates to all peptides having preferably 60%, 70%, 80%, especially preferably 90% homology to the sequence in accordance with SEQ ID NO 1. It will be appreciated that these homologs can be modified by deletion, addition, substitution, translocation, inversion and/ or insertion. More specifically, this modification concerns homologous peptides with functional analogy. In the meaning of the invention the peptides are functionally analogous if they specifically interact with autoantibodies associated with the above-mentioned diseases.

Accordingly, the invention is directed to the disclosed peptide and to the homologs which can be used in a functionally analogous manner. With respect to homologs/functional analogs, it will be appreciated by those skilled in the art that modifications by additions, deletions or substitutions can be made without substantially changing the polypeptide. The modified amino acid sequence is not substantially changed if it achieves the same function as the sequence in accordance with SEQ ID NO 1 in essentially the same way, leading to the same result. For example, functionally analogous peptides can be SEQ ID NO 2:

MPHLMERMVGSGLLWLALVSCILTQASAVQRGYGNPIEASSYGLDLDCGA

PGTPEAHVCFDPCQNYTLLDEPFRSTENSAGSQGCDKNMSGWYRFVGEGG

VRMSETCVQVHRCQTDAPMWLNGTHPALGDGITNHTACAHWSGNCCFWKT

EVLVKACPGGYHVYRLEGTPWCNLRYCTVPRDPSTVEDKCEKACRPEEEC

LALNSTWGCFCRQDLNSSDVHSLQPQLDCGPREIKVKVDKCLLGGLGLGE

EVIAYLRDPNCSSILQTEERNWVSVTSPVQASACRNILERNQTHAIYKNT

LSLVNDFIIRDTILNINFQCAYPLDMKVSLQAALQPIVSSLNVSVDGNGE

FIVRMALFQDQNYTNPYEGDAVELSVESVLYVGAILEQGDTSRFNLVLRN

CYATPTEDKADLVKYFIIRNSCSNQRDSTIHVEENGQSSESRFSVQMFMF

AGHYDLVFLHCEIHLCDSLNEQCQPSCSRSQVRSEVPAIDLARVLDLGPI

TRRGAQSPGVMNGTPSTAGFLVAWPMVLLTVLLAWLF or SEQ ID NO 3

MPHLMERMVGSGLLWLALVSCILTQASAVQRGYGNPIEASSYGLDLD

CGAPGTPEAHVCFDPCQNYTLLDEPFRSTENSAGSQGCDKNMSGWYR

FVGEGGVRMSETCVQVHRCQTDAPMWLNGTHPALGDGITNHTACAHW

SGNCCFWKTEVLVKACPGGYHVYRLEGTPWCNLRYCTDPSTVEDKCE

KACRPEEECLALNSTWGCFCRQDLNSSDVHSLQPQLDCGPREIKVKV

DKCLLGGLGLGEEVIAYLRDPNCSSILQTEERNWVSVTSPVQASACR

NILERNQTHAIYKNTLSLVNDFIIRDTILNINFQCAYPLDMKVSLQA

ALQPIVSSLNVSVDGNGEFIVRMALFQDQNYTNPYEGDAVELSVESV

LYVGAILEQGDTSRFNLVLRNCYATPTEDKADLVKYFIIRNSCSNQR

DSTIHVEENGQSSESRFSVQMFMFAGHYDLVFLHCEIHLCDSLNEQC

QPSCSRSQVRSEVPAIDLARVLDLGPITRRGAQSPGVMNGTPSTAGF

LVAWPMVLLTVLLAWLF or SEQ ID NO 4

MPHLMERMVGSGLLWLALVSCILTQASAVQRVPRDPSTVEDKCEKAC

RPEEECLALNSTWGCFCRQDLNSSDVHSLQPQLDCGPREIKVKVDKC

LLGGLGLGEEVIAYLRDPNCSSILQTEERNWVSVTSPVQASACRNIL

ERNQTHAIYKNTLSLVNDFIIRDTILNINFQCAYPLDMKVSLQAALQ

PIVSSLNVSVDGNGEFIVRMALFQDQNYTNPYEGDAVELSVESVLYV

GAILEQGDTSRFNLVLRNCYATPTEDKADLVKYFIIRNSCSNQRDST

IHVEENGQSSESRFSVQMFMFAGHYDLVFLHCEIHLCDSLNEQCQPS

CSRSQVRSEVPAIDLARVLDLGPITRRGAQSPGVMNGTPSTAGFLVA

WPMVLLTVLLAWLF or SEQ ID NO 5

MPHLMERMVGSGLLWLALVSCILTQASAVQRDPSTVEDKCEKACRPE

EECLALNSTWGCFCRQDLNSSDVHSLQPQLDCGPREIKVKVDKCLLG

GLGLGEEVIAYLRDPNCSSILQTEERNWVSVTSPVQASACRNILERN

QTHAIYKNTLSLVNDFIIRDTILNINFQCAYPLDMKVSLQAALQPIV

SSLNVSVDGNGEFIVRMALFQDQNYTNPYEGDAVELSVESVLYVGAI

LEQGDTSRFNLVLRNCYATPTEDKADLVKYFIIRNSCSNQRDSTIHV

EENGQSSESRFSVQMFMFAGHYDLVFLHCEIHLCDSLNEQCQPSCSR

SQVRSEVPAIDLARVLDLGPITRRGAQSPGVMNGTPSTAGFLVAWPM

VLLTVLLAWLF

More specifically, the above-mentioned peptides are claimed for the diagnosis of the immune diseases specified above. The above-mentioned sequences accomplish essentially the same function in essentially the same way and furnish essentially the same result as sequence SEQ ID NO 1. They are therefore covered by the teaching according to the invention, i.e., the use of the GP2 molecule as a drug, especially in the prophylaxis, diagnosis, therapy and/or aftercare of inflammatory bowel diseases.

Consequently, the amino acid sequences, i.e. the peptides in the meaning of the invention, may include a number of additional amino acids, spacers or other structures that makes them suitable for interaction with autoantibodies, preferably in such a way that they represent an epitope for the latter. Accordingly, the sequence according to the invention is not restricted to peptides related to anti-body epitopes but rather refers to the molecule and all fragments thereof specifically interacting with autoantibodies in such a way that diagnosis of inflammatory bowel diseases is possible. In the meaning of the invention the terms epitope, peptide and amino acid sequence can therefore be used synonymously in preferred embodiments.

Various ways of preparing functionally analogous peptides have been disclosed in the prior art. Peptides designed starting from the peptides of the invention using such methods are included in the teaching according to the invention. For example, one way of generating functionally analogous peptides has been described in PNAS USA 1998, Oct. 13, 9521, 12179-84; WO 99/6293 and/or WO 02/38592; the above teachings are hereby incorporated in the disclosure of the invention. That is, all peptides, peptide fragments or structures comprising peptides generated using the methods mentioned above—starting from the peptides of the invention—are peptides according to the invention, provided they accomplish the object of the invention and, in particular, interact with the pathogenic autoantibodies. For example, these autoantibodies can be agonistic autoantibodies activating receptors.

In another preferred embodiment of the invention the molecule comprises a linker or spacer selected from the group of α-aminocarboxylic acids as well as homo- and heterooligomers thereof, α,ω-aminocarboxylic acids and branched homo- or heterooligomers thereof, other amino acids, as well as linear and branched homo- or heterooligomers; aminooligoalkoxyalkylamines; maleinimidocarboxylic acid derivatives; oligomers of alkylamines; 4-alkylphenyl derivatives; 4-oligoalkoxyphenyl or 4-oligoalkoxyphenoxy derivatives; 4-oligoalkylmercaptophenyl or 4-oligoalkylmercaptophenoxy derivatives; 4-oligoalkylaminophenyl or 4-oligoalkylaminophenoxy derivatives; (oligoalkylbenzyl)phenyl or 4-(oligoalkylbenzyl)phenoxy derivatives, as well as 4-(oligoalkoxybenzyl)phenyl or 4-(oligoalkoxybenzyl)phenoxy derivatives; trityl derivatives; benzyloxyaryl or benzyloxyalkyl derivatives; xanthen-3-yloxyalkyl derivatives; (4-alkylphenyl)- or co-(4-alkylphenoxy)alkanoic acid derivatives; oligoalkylphenoxyalkyl or oligoalkoxyphenoxyalkyl derivatives; carbamate derivatives; amines; trialkylsilyl or dialkylalkoxysilyl derivatives; alkyl or aryl derivatives or combinations thereof.

In another preferred embodiment of the invention the GP2 molecule is used as a soluble or solid phase-bound autoantigen for direct or indirect autoantibody detection in stool and/or body fluids, especially blood and/or serum, in which case the use of the GP2 molecule in accordance with SEQ ID NO 1 was found particularly advantageous.

In another preferred embodiment of the invention the sequences according to the present application, or the peptides which can be generated therefrom, are immobilized. More specifically, the solid phase-bound GP2 molecule in accordance with SEQ ID NO 1 is bound to organic, inorganic, synthetic and/or mixed polymers, preferably agarose, cellulose, silica gel, polyamides and/or polyvinyl alcohols. In the meaning of the invention, immobilization is understood to involve various methods and techniques to fix the peptides on specific carriers, e.g. according to WO 99/56126 or WO 02/26292. For example, immobilization can serve to stabilize the peptides so that their activity would not be reduced or adversely modified by biological, chemical or physical exposure, especially during storage or in single-batch use. Immobilization of the peptides allows repeated use under technical or clinical routine conditions; furthermore, a sample—preferably blood components—can be reacted with at least one of the peptides according to the invention in a continuous fashion. In particular, this can be achieved by means of various immobilization techniques, with binding of the peptides to other peptides or molecules or to a carrier proceeding in such a way that the three-dimensional structure—particularly in the active center mediating the interaction with the autoantibodies—of the corresponding molecules, especially of said peptides, would not be changed. Advantageously, there is no loss in specificity to the autoantibodies of patients as a result of such immobilization. In the meaning of the invention, three basic methods can be used for immobilization:

(i) Crosslinking: in crosslinking, the peptides are fixed to one another without adversely affecting their activity. Advantageously, they are no longer soluble as a result of such crosslinking.

(ii) Binding to a carrier: binding to a carrier proceeds via adsorption, ionic binding or covalent binding, for example. Such binding may also take place inside microbial cells or liposomes or other membranous, closed or open structures. Advantageously, the peptides are not adversely affected by such fixing. For example, multiple or continuous use of carrier-bound peptides is possible with advantage in clinical diagnosis or therapy.

(iii) Inclusion: inclusion in the meaning of the invention especially proceeds in a semipermeable membrane in the form of gels, fibrils or fibers. Advantageously, encapsulated peptides are separated from the surrounding sample solution by a semipermeable membrane in such a way that interaction with the autoantibodies or fragments thereof still is possible. Various methods are available for immobilization, such as adsorption on an inert or electrically charged inorganic or organic carrier. For example, such carriers can be porous gels, aluminum oxide, bentonite, agarose, starch, nylon or polyacrylamide. Immobilization proceeds via physical binding forces, frequently involving hydrophobic interactions and ionic binding. Advantageously, such methods are easy to handle and have little influence on the conformation of the peptides. Advantageously, binding can be improved as a result of electrostatic binding forces between the charged groups of the peptides and the carrier, e.g. by using ion exchangers, particularly Sephadex.

Another method is covalent binding to carrier materials. In addition, the carriers may have reactive groups forming homopolar bonds with amino acid side chains. Suitable groups in peptides are carboxy, hydroxy and sulfide groups and especially the terminal amino groups of lysines. Aromatic groups offer the possibility of diazo coupling. The surface of microscopic porous glass particles can be activated by treatment with silanes and subsequently reacted with peptides. For example, hydroxy groups of natural polymers can be activated with bromocyanogen and subsequently coupled with peptides. Advantageously, a large number of peptides can undergo direct covalent binding with polyacrylamide resins. Inclusion in three-dimensional networks involves inclusion of the peptides in ionotropic gels or other structures well-known to those skilled in the art. More specifically, the pores of the matrix are such in nature that the peptides are retained, allowing interaction with the target molecules. In crosslinking, the peptides are converted into polymer aggregates by crosslinking with bifunctional agents. Such structures are gelatinous, easily deformable and, in particular, suitable for use in various reactors. By adding other inactive components such as gelatin in crosslinking, advantageous improvement of mechanical and binding properties is possible. In microencapsulation, the reaction volume of the peptides is restricted by means of membranes. For example, microencapsulation can be carried out in the form of an interfacial polymerization. Owing to the immobilization during microencapsulation, the peptides are made insoluble and thus reusable. In the meaning of the invention, immobilized peptides are all those peptides being in a condition that allows reuse thereof. Restricting the mobility and solubility of the peptides by chemical, biological or physical means advantageously results in lower process cost, particularly when eliminating autoantibodies from blood components.

In another preferred embodiment of the invention, unspecific adsorber molecules selected from the group comprising protein A, protein G, anti-human immunoglobulins or L-tryptophan are employed in addition to the soluble or solid phase-bound GP2 molecule in accordance with SEQ ID NO 1.

In another preferred embodiment of the invention the GP2 molecule in accordance with SEQ ID NO 1 is selected from the group comprising:

a) a molecule having an amino acid sequence which has sufficient homology to the GP2 molecule in accordance with SEQ ID NO 1 to be functionally analogous thereto;
b) a molecule according to a) which has been modified by deletion, addition, substitution, translocation, inversion and/or insertions and is functionally analogous to the molecule according to a).

Surprisingly, the use of the homologous and modified GP2 molecules in accordance with SEQ ID NO 1 is associated with a number of advantages. In practice it was found that the changes according to b) allow to obtain molecules which have increased stability, thus resulting in advantages in the laboratory daily routine.

In another preferred embodiment of the invention the molecule specified under b) has at least 40% homology to the molecule specified under a). In laboratory daily routine said 40% homologs have the surprising effect of not only being storable longer than molecules according to a) in general, but also of having an increased tolerance to temperature fluctuations.

In another preferred embodiment of the invention the molecule specified under b) has at least 60%, preferably 70%, more preferably 80%, especially preferably 90% homology to the molecule specified under a). Regarding all molecules according to b), the advantage of this variant is the completely surprising property of having the longest storage life.

In another preferred embodiment of the invention the GP2 molecule in accordance with SEQ ID NO 1 is in a linear or cyclic form, peptide cyclization proceeding via disulfide bridges when two cysteines are present or by way of amide cyclization which optionally proceeds via the side chains, terminal C and N or a combination of these possible ways. In the above-mentioned methods, this variant of the GP2 molecule can result in increased stability of the GP2 molecule in the presence of various denaturing buffers.

In another aspect the invention relates to the use of GP2 in accordance with SEQ ID NO 1 in the production of a column with coupled GP2 for the treatment of inflammatory bowel diseases, especially Crohn's disease, chronic pancreatitis and/or ulcerative colitis, said treatment comprising passing the plasma of a patient over the column, with conditions being selected which allow effective binding of GP2 to the immunoglobulins in the plasma of the patient, thereby removing a significant amount of immunoglobulins from the plasma of the patient, and returning the plasma thus obtained into the patient. The above use has the advantageous effect that immunoglobulins can be removed extremely rapidly from the blood of IBD patients in acute cases.

In another aspect the invention relates to an immunogenic agent using GP2, immunoreactive sequences or analogs thereof in the production of a medicament for use in the diagnosis or therapy control of diseases associated with an immune reaction against these substances. Surprisingly, the above-described sequences of GP2 also enable the production of easy-to-handle medications which can be taken or used by the patient according to the physician's instructions so that in-hospital treatment is not required.

In a preferred embodiment the invention is directed to the use of the above-mentioned immunogenic agent in diagnosis or therapy control of chronic inflammatory or autoimmune diseases, particularly inflammatory bowel diseases such as Crohn's disease, chronic pancreatitis and/or ulcerative colitis. The advantage of this embodiment is that even those patients with autoimmune inflammatory bowel diseases who barely have access to diagnostic and therapeutic centers of competence can obtain an easy-to-handle medication and use it under the supervision of a family doctor.

In a preferred fashion the sequence SEQ ID NO 1 of GP2 according to the present application, immunoreactive sequences, analogs or fragments thereof are used as therapeutic active substances in the production of a medicament and applied in an oral therapy of diseases associated with an immune reaction against these substances. Use as therapeutic active substance in the meaning of the invention implies the use of the amino acid sequence or peptides which can be formed therefrom in the entire field of medicine. Advantageously, GP2 is a sufficiently stable and absorbable peptide so that it can be administered to patients as medicament even on the oral route.

The invention also relates to a pharmaceutical composition comprising at least one GP2 molecule in accordance with SEQ ID NO 1, optionally together with a pharmaceutically acceptable carrier, for the treatment of chronic inflammatory or autoimmune diseases, particularly inflammatory bowel diseases such as Crohn's disease, chronic pancreatitis and/or ulcerative colitis.

In particular, the pharmaceutical composition can be used as a drug. To this end, it is possible, for example, to modify the peptides or the entire amino acid sequence by means of cyclization or other procedures well-known to those skilled in the art such that destruction thereof by endogenous peptide-degrading structures, e.g. serum proteases, is prevented. By using the peptides or the protein (SEQ ID NO 1) according to the invention, in vivo or ex vivo neutralization of autoantibodies is possible. In in vivo neutralization, the drugs are administered directly to the patient; in ex vivo neutralization, the blood is conducted out of the body e.g. via a loop, e.g. in the form of a tube circulation, subsequently contacted with the drug and, following neutralization of the autoantibodies, returned into the organism, i.e., the patient. Regarded as drugs in the meaning of the invention are compositions for therapeutic and prophylactic purposes, as well as pharmaceutical compositions usable as diagnostic agents.

According to the invention, drugs or pharmaceutical compositions—used in a synonymous fashion herein—are substances and formulations of substances intended to cure, alleviate or avoid diseases, illness, physical defects or pathological affection by application on or in the human body. According to the invention, medical adjuvants are substances used as active ingredients in the production of drugs. Pharmaceutical-technical adjuvants serve to suitably formulate the drug or pharmaceutical composition and, if required during the production process only, can even be removed thereafter, or they can be part of the pharmaceutical composition as pharmaceutically tolerable carriers. Examples of pharmaceutically tolerable carriers will be given below. Drug formulation or formulation of the pharmaceutical composition is optionally effected in combination with a pharmaceutically tolerable carrier and/or diluent. Examples of suitable pharmaceutically tolerable carriers are well-known to those skilled in the art and comprise e.g. phosphate-buffered saline, water, emulsions such as oil/water emulsions, various types of detergents, sterile solutions, and so forth. Drugs or pharmaceutical compositions comprising such carriers can be formulated by means of well-known conventional methods. These drugs or pharmaceutical compositions can be administered to an individual at a suitable dose, e.g. in a range of from 1 μg to 10 g of peptides or protein per day and patient. Doses of from 1 mg to 1 g are preferred. Preferred is administration of doses as small in number and as low as possible, preferably a single dose. Administration can be effected on various routes, e.g. intravenous, intraperitoneal, intrarectal, intragastrointestinal, intranodal, intramuscular, local, but also subcutaneous, intradermal or on the skin or via mucosa.

Administration of nucleic acids encoding the peptide according to the invention can also be effected in the form of a gene therapy, e.g. via viral vectors. The kind of dosage and route of administration can be determined by the attending physician according to clinical factors. As is familiar to those skilled in the art, the kind of dosage will depend on various factors such as size, body surface, age, sex, or general health condition of the patient, but also on the particular agent being administered, the time period and type of administration, and on other medications possibly administered in parallel. Those skilled in the art will also be familiar with the fact that the concentration of autoantibodies can be diagnosed first, using the peptides according to the invention, in order to determine the required concentration of drug.

More specifically, the pharmaceutical compositions or drugs comprise a pharmacological substance which includes one or more peptides or the protein according to the invention or/and nucleic acid molecules encoding the same, in a suitable solution or administration form. Administration thereof can be effected either alone or together with appropriate adjuvants described in connection with drugs or pharmaceutical compositions, or in combination with one or more adjuvants, e.g. QS-21, GPI-0100 or other saponines, water-oil emulsions such as Montanide adjuvants, polylysine, polyarginine compounds, DNA compounds such as CpG, Detox, bacterial vaccines such as typhoid vaccines or BCG vaccines, salts such as calcium phosphates and/or other suitable material enhancing the effect, preferably immunostimulatory molecules such as interleukins, e.g. IL-2, IL-12, IL-4 and/or growth factors such as GM-CSF. They are mixed with the peptides or recognition molecules of the invention according to well-known methods and administered in suitable formulations and dosages. Formulations, dosages and suitable components are well-known to those skilled in the art.

Obviously, the pharmaceutical composition or drug can also be a combination of two or more of the inventive pharmaceutical compositions or drugs, as well as a combination with other drugs, such as antibody therapies, chemotherapies or radiotherapies, suitably administered or applied at the same time or separately in time. The production of the drugs or pharmaceutical compositions proceeds according to per se known methods.

As envisaged in a preferred embodiment of the invention, the pharmaceutical carrier for the pharmaceutical agent is selected from the group comprising fillers, disintegrants, binders, humectants, diluents, dissolution retarders, absorption enhancers, wetting agents, absorbents and/or lubricants. Surprisingly, it was found in practice that, advantageously, a large number of pharmaceutical carriers are suitable for GP2 so that the administration form of the drug can largely be adapted to the patient's desires.

The invention also relates to a diagnostic kit for the determination of autoimmune diseases, comprising a GP2 molecule in accordance with SEQ ID NO 1. The diagnostic kit optionally includes instructions concerning combining the contents of the kit and/or providing a formulation for the detection of inflammatory bowel diseases, particularly Crohn's disease, chronic pancreatitis and/or ulcerative colitis. For example, the instruction can be in the form of an instruction leaflet or other medium providing the user with information as to the type of method wherein the substances mentioned are to be used. Obviously, the information need not necessarily be in the form of an instruction leaflet, and the information may also be imparted via the Internet, for example. To a patient, one advantageous effect of such a kit is, for instance, that he or she, without directly addressing a physician, can determine the actual state of a disease even during a journey and optionally adapt diet and activities accordingly.

The invention also relates to an apparatus for chromatography, especially for apheresis, comprising the GP2 molecule in accordance with SEQ ID NO 1 for the treatment of inflammatory bowel diseases, especially Crohn's disease, chronic pancreatitis and/or ulcerative colitis. As a rule, traditional treatment of acute inflammations envisages control of the intestinal inflammation as rapid as possible, using a drug-based treatment. The advantage of the chromatographic apparatus according to the invention is that the patient need not be administered with drugs, but instead, purification of the patient's blood from antibodies—thereby preventing extension from the center of inflammation—is effected on the apheresis column without the risk of drug interactions and impairment of organs. In a preferred embodiment the GP2 molecule in accordance with SEQ ID NO 1 is bound to a solid phase inside the chromatographic system. The GP2 molecules have surprisingly high affinity to the autoantibodies and show good immobilization on a solid phase so that the apparatus according to the invention can be used to eliminate the autoantibodies from fluids of a patient or neutralize the autoantibodies. This method is known to those skilled in the art under the term of immunoadsorption and apheresis therapy. With the aid of immunoadsorption, immunoglobulins are removed from the blood of a patient.

Advantageously, this immunoadsorption treatment can be conducted both as inhospital and ambulant treatment. It can be envisaged that the apparatus, particularly the so-called adsorber, is part of an extracorporeal blood circulation. To this end, blood is taken continuously or discontinuously from a patient's major vessel, particularly from an arm vein, and separated into single components, such as cellular and humoral components, using filtration or centrifugation. In particular, one essential blood component obtained in this fashion is blood plasma. Advantageously, the blood plasma can be passed through the apparatus of the invention and, following adsorption of the autoantibodies, returned into the patient, particularly through another vein of arms or legs, together with previously separated blood components, especially cellular components. It can also be envisaged that the peptides are immobilized on a Sepharose matrix. The matrix can be placed in a container having a volume of 10 to 400 ml. Thereafter, the blood plasma of the patient can be passed over the matrix where the autoantibodies will be bound, thus allowing elimination thereof from the blood plasma.

Those skilled in the art will be familiar with various ways of providing such solid phase-fixed peptides, e.g. in the form of (i) regeneratable adsorption columns, (ii) double columns and (iii) disposable columns. The diverse wash and elution solutions permitting high efficiency of treatment can easily be determined by a person skilled in the art by using routine tests. By providing the teaching according to the invention, particularly the peptides of the invention, various ways of employing the peptides in vivo, ex vivo and in vitro in prophylaxis, diagnosis, therapy and aftercare of cold-induced, autoantibody-mediated diseases are disclosed to a person skilled in the art.

The teaching according to the present application is remarkable for the following features:
  Departure from conventional technologies
  New field of problems
  Existence of a long-unsatisfied, urgent need for the solution of the problem solved by the invention Hitherto vain efforts in the art Simplicity of a solution indicates inventive activity, especially as it replaces more complicated teachings Development in scientific technology has proceeded in a different direction Achievement that rationalizes development Erroneous ideas in the art on the solution of the problem at issue (prejudice)

Technical progress, e.g. improvement, performance enhancement, lower expense, savings of time, materials, work steps, cost or raw materials difficult to obtain, enhanced reliability, elimination of flaws, superior quality, maintenance freedom, greater efficiency, higher yield, expansion of the technical scope, provision of a further means, creation of a second approach, creation of a new field, first-time solution of a problem, reserve means, alternatives, scope for rationalization, automation or miniaturization, or enrichment of the range of available drugs Fortunate choice (out of a variety of possibilities, one has been selected, the result of which has not been predictable, making it a patentable fortunate choice)

Error in prior art references

Young field of technology

Combination invention, i.e., several known elements have been combined to achieve a surprising effect Issue of licenses Praise in the art Economic success These properties apply especially to the preferred embodiments of the invention.

Without intending to be limiting, the invention will be explained in more detail with reference to an example.

METHODS

Purification of GP2 from Rat Pancreas
Obtaining Zymogen Granules (ZG) and Purification of the ZG Membranes All of the following working steps were carried out in an ice bath or with cooling to 4° C. The pancreata of four grown Wistar rats (about 2.4 g of tissue) were mechanically reduced in size and macerated in a tenfold volume of ice-cold 0.3 M saccharose solution in a POTTER homogenizer (2 strokes at 1000 rpm and 2 strokes at 1300 rpm). The macerated material was subsequently filtered over a gauze cloth. Cell debris and nuclei were removed by centrifugation at 500 g for 10 min. Using centrifugation at 3000 g for 10 min, the zymogen granules (lower, white solid pellet) and the mitochondria (overlying, loose brownish pellet) were deposited from the supernatant. The mitochondria were carefully washed off with buffer A (10 mM morpholinopropanesulfonic acid (MOPS), pH 6.8), and the zymogen granules were resuspended in 2 ml of 0.1 M sodium carbonate solution, 1 mM diisopropyl fluorophosphate (DFP), using a vortexer. The granules were lysed in an ice bath for 1 hour. The lysis batch was layered on a discontinuous saccharose gradient (0.3 M/1 M) and centrifuged at 200,000 g for 90 min. The membrane fraction accumulated as a band in the density interface. The band was sucked off and the resulting solution adjusted to 0.3 M sodium bromide. The membranes were sedimented by centrifugation at 200,000 g for 60 min.

Solubilization of GP2

The resulting membrane pellet was resuspended in 0.5 ml of buffer B (20 mM morpholinoethanesulfonic acid (MES), pH 7.0; 80 mM KCl; 45 g/ml saponine) using ultrasound and, following addition of phosphatidylinositol-specific phospholipase C (*B. cereus*), GP2 was removed from the membrane by incubation at 37° C. for 1 hour. The membranes were pelleted by centrifugation (200,000 g, 60 min), and the supernatant including soluble GP2 was concentrated about 1:5 using ultrafiltration.

Enzyme-Linked Immunosorbent Assay (ELISA) for the Determination of GP2 Antibodies Microtiter plates (Maxisorb, Nunc, Roskilde) were coated with a solution of 10 µg/ml rat GP2 in coating buffer (100 mM Na carbonate, pH 9.6) with 50 µl/well at 4° C. overnight. After washing the microtiter plate with wash buffer (10 mM Na phosphate, 150 mM NaCl, 0.1% Tween 20, pH 7.4), the wells were incubated with 300 ml of blocking solution (wash buffer, 1% bovine serum albumin (BSA), pH 7.4) at room temperature (RT) for 30 min. Thereafter, the wells were washed three times with wash buffer, and 50 ml of human serum samples per well, diluted 1:100 in dilution buffer (10 mM Na phosphate, 150 mM NaCl, 1% RSA), were incubated at RT for 60 min. After washing three times with dilution buffer, the wells were filled with 50 ml of conjugate solution (anti-human IgG peroxidase, sheep, 1 µg/ml, dilution buffer) and incubated at RT for 30 min. The wells were subsequently washed another three times, and 50 ml of substrate solution (tetramethylbenzidine) was dispensed per well. After incubating at RT for 10 min, the substrate reaction was terminated by adding 50 ml of quenching solution (0.3 M sulfuric acid). The optical density of the solution in each well was measured bichromatically at 450 nm and 620 nm using a microtiter plate photometer, followed by computer-based assessment using the EIAstar software program.

Indirect Immunofluorescence (IIF) for the Determination of Pancreas Antigen Antibodies Commercial monkey pancreas sections (Euroimmun, Lubeck) were used to determine pancreas antigen antibodies by means of IIF. The serum samples were diluted 1:40, 1:80 and 1:160 with dilution buffer. 25 µl of diluted serum was pipetted on each reaction pad of the reagent support, and the microscope slides with the tissue sections were incubated at RT for 30 min. Thereafter, the slides were washed with phosphate buffer for 1 min. 20 ml of labelled antiserum (anti-human IgG FITC) was pipetted on each pad of the cleaned reagent support and incubated with the tissue sections on the slides at RT for 30 min. After washing once more with phosphate buffer for 1 min, coverslips were placed on the slides with the aid of a mounting medium. Fluorescence evaluation was performed using a fluorescence microscope.

LITERATURE

Bossuyt X. Serologic markers in inflammatory bowel disease. Clin Chem 2006, 52 (2): 171-181.

Fukuoka S-I. Molecular cloning and sequences of cDNAs encoding α (large) and β (small) isoforms of human pancreatic zymogen granule membrane-associated protein GP2. BBA 2000, 1491, 376-380.

Fricke H, Birkhofer A, Folwaczny C, Meister W, Scriba P C. Characterization of antigens from the human exocrine pancreatic tissue (Pag) relevant as target antigens for autoantibodies in Crohn's disease. Eur J Clin Invest, 1999, 29: 41-45.

WO 01/94409 (CORIXA CORP [US]; Hirst Shannon K [US]; Harlocker Susan L [US]; Dillon) Dec. 13, 2001 (Dec. 13, 2001) Compositions and methods for the therapy and diagnosis of pancreatic cancer.

Main J, McKenzie H, Yeaman G R, Kerr M A, Robson D, Pennington C R, Parratt D. Anti-body to *saccharomyces cerevisiae* (bakers' yeast) in Crohn's disease. BMJ, 297: 1105-1106.

Mayet W J, Press A G, Hermann E, Moll R, Manns M, Ewe K, Meyer zum Büschenfelde K H. Antibodies to cytoskeletal proteins in patients with Crohn's disease. Eur J Clin Invest, 1990, 20: 516-524.

Seibold F, Weber P, Jenss H, Wiedmann K H. Antibodies to a trypsin sensitive pancreatic antigen in chronic inflammatory bowel disease: specific markers for a subgroup of patients with Crohn's disease. Gut 1991, 32: 1192-1197.

WO 96/17873 A (Alphagene INC [US]) Jun. 13, 1996 (Jun. 13, 1996) Diagnosis of pancreatitits.

Stöcker W, Otte M, Ulrich S, Normann D, Finkbeiner H, Stöcker K, Jantschek G, Scriba P C. Autoimmunity to pancreatic juice in Crohn's disease. Results of an autoantibody screening in patients with chronic inflammatory bowel disease. Scand J Gastroenterol, 1987, 22 (suppl 139), 41-52.

---

The invention claimed is:

1. A method for detection of autoantibodies from stool and/or body fluids comprising:
providing (i) GP2 molecules comprising SEQ ID NO: 1, or (ii) GP2 molecules with an amino acid sequence having at least 80% homology with SEQ ID NO: 1,
contacting said GP2 molecules with said autoantibodies from stool and/or body fluids,
detecting the autoantibodies that bind said GP2 molecules in an immune reaction, wherein an inflammatory intestinal disease is diagnosed via said immune reaction.

2. The method according to claim 1, wherein said autoantibodies are human IgA, IgM and/or IgG antibodies.

3. The method according to claim 1, wherein the GP2 molecule is of human, animal, recombinant or synthetic origin.

4. The method according to claim 2, wherein the detecting is carried out in an immunoassay, preferably with direct or indirect coupling of one reactant to a labelling substance.

5. A method according to claim 1 wherein the inflammatory intestinal disease is Crohn's disease, and wherein said immune reaction is carried out without using tissue sections of animal or human tissue.

6. The method according to claim 1, wherein the detecting is carried out in an immunoassay, preferably using direct or indirect coupling of a reactant with a labelling substance, excluding immunofluorescence tests on the basis of tissue sections.

7. The method according to claim 1, wherein detecting is carried out on a solid phase.

8. The method of claim 1, wherein the GP2 molecule comprises a linker and/or spacer selected from the group consisting of α-aminocarboxylic acids as well as homo- and heterooligomers thereof, α,ω-okaminocarboxylic acids and branched homo- or heterooligomers thereof; other amino acids, as well as linear and branched homo- or heterooligomers; amino-oligoalkoxyalkylamines; maleinimidocarboxylic acid derivatives; oligomers of alkylamines; 4-alkylphenyl derivatives; 4-oligoalkoxyphenyl or 4-oligoalkoxyphenoxy derivatives; 4-oligoalkylmercapto-phenyl or 4-oligoalkylmercaptophenoxy derivatives; 4-oligoalkylaminophenyl or 4-oligoalkylaminophenoxy derivatives; (oligoalkylbenzyl)phenyl or 4-(oligoalkylbenzyl)phenoxy derivatives, as well as 4-(oligoalkoxybenzyl)phenyl or 4-(oligoalkoxybenzyl)phenoxy derivatives; trityl derivatives; benzyloxyaryl or benzyloxyalkyl derivatives; xanthen-3-yloxyalkyl derivatives; (4-alkylphenyl)- or ω-(4-alkylphenoxy)alkanoic acid derivatives; oligoalkylphenoxyalkyl or oligoalkoxyphenoxyalkyl derivatives; carbamate derivatives; amines; trialkylsilyl or dialkylalkoxysilyl derivatives; alkyl or aryl derivatives and/or combinations thereof.

9. The method of claim 1, wherein the GP2 molecules are in soluble form or bound to a solid phase in direct or indirect autoantibody detection in stool and/or body fluids, especially blood and/or serum.

10. The method of claim 9, wherein the solid phase-bound GP2 molecules comprising SEQ ID NO:1 is bound to organic, inorganic, synthetic and/or mixed polymers, preferably agarose, cellulose, silica gel, polyamides and/or polyvinyl alcohols.

11. The method of claim 9, further providing protein A, protein G, anti-human immunoglobulins or L-tryptophan.

12. The method of claim 1, wherein the GP2 molecules is in a linear or cyclic form, peptide cyclization proceeding via disulfide bridges when two cysteines are present or by way of amide cyclization which optionally proceeds via the side chains, terminal C and N or a combination of these possible ways.

13. The method of claim 1, wherein said antibodies are detected in blood and/or serum.

14. The method of claim 1, wherein said antibodies are detected in stool.

15. The method of claim 1, wherein the diagnosis is performed ex vivo.

16. The method of claim 1, wherein said amino acid sequence has at least 90% homology with SEQ ID NO: 1.

* * * * *

SEQUENCE LISTING

```
<160> NUMBER OF SEQ ID NOS: 5

<210> SEQ ID NO 1
<211> LENGTH: 527
<212> TYPE: PRT
<213> ORGANISM: Homo sapiens
<220> FEATURE:
<221> NAME/KEY: MISC_FEATURE
<223> OTHER INFORMATION: Glykoprotein 2

<400> SEQUENCE: 1
```

Met Val Gly Ser Gly Leu Leu Trp Leu Ala Leu Val Ser Cys Ile Leu
1               5                   10                  15

Thr Gln Ala Ser Ala Val Gln Arg Gly Tyr Gly Asn Pro Ile Glu Ala
            20                  25                  30

Ser Ser Tyr Gly Leu Asp Leu Asp Cys Gly Ala Pro Gly Thr Pro Glu
        35                  40                  45

Ala His Val Cys Phe Asp Pro Cys Gln Asn Tyr Thr Leu Leu Asp Glu
    50                  55                  60

Pro Phe Arg Ser Thr Glu Asn Ser Ala Gly Ser Gln Gly Cys Asp Lys
65                  70                  75                  80

Asn Met Ser Gly Trp Tyr Arg Phe Val Gly Glu Gly Gly Val Arg Met
                85                  90                  95

Ser Glu Thr Cys Val Gln Val His Arg Cys Gln Thr Asp Ala Pro Met
            100                 105                 110

Trp Leu Asn Gly Thr His Pro Ala Leu Gly Asp Gly Ile Thr Asn His
        115                 120                 125

Thr Ala Cys Ala His Trp Ser Gly Asn Cys Cys Phe Trp Lys Thr Glu
    130                 135                 140

Val Leu Val Lys Ala Cys Pro Gly Gly Tyr His Val Tyr Arg Leu Glu
145                 150                 155                 160

Gly Thr Pro Trp Cys Asn Leu Arg Tyr Cys Thr Asp Pro Ser Thr Val
                165                 170                 175

Glu Asp Lys Cys Glu Lys Ala Cys Arg Pro Glu Glu Cys Leu Ala
            180                 185                 190

Leu Asn Ser Thr Trp Gly Cys Phe Cys Arg Gln Asp Leu Asn Ser Ser
        195                 200                 205

Asp Val His Ser Leu Gln Pro Gln Leu Asp Cys Gly Pro Arg Glu Ile
    210                 215                 220

Lys Val Lys Val Asp Lys Cys Leu Leu Gly Leu Gly Leu Gly Glu
225                 230                 235                 240

Glu Val Ile Ala Tyr Leu Arg Asp Pro Asn Cys Ser Ser Ile Leu Gln
                245                 250                 255

Thr Glu Glu Arg Asn Trp Val Ser Val Thr Ser Pro Val Gln Ala Ser
            260                 265                 270

Ala Cys Arg Asn Ile Leu Glu Arg Asn Gln Thr His Ala Ile Tyr Lys

|     |     |     |     |     | 275 |     |     |     | 280 |     |     |     |     | 285 |     |

Asn Thr Leu Ser Leu Val Asn Asp Phe Ile Ile Arg Asp Thr Ile Leu
290                 295                 300

Asn Ile Asn Phe Gln Cys Ala Tyr Pro Leu Asp Met Lys Val Ser Leu
305                 310                 315                 320

Gln Ala Ala Leu Gln Pro Ile Val Ser Ser Leu Asn Val Ser Val Asp
            325                 330                 335

Gly Asn Gly Glu Phe Ile Val Arg Met Ala Leu Phe Gln Asp Gln Asn
            340                 345                 350

Tyr Thr Asn Pro Tyr Glu Gly Asp Ala Val Glu Leu Ser Val Glu Ser
            355                 360                 365

Val Leu Tyr Val Gly Ala Ile Leu Glu Gln Gly Asp Thr Ser Arg Phe
370                 375                 380

Asn Leu Val Leu Arg Asn Cys Tyr Ala Thr Pro Thr Glu Asp Lys Ala
385                 390                 395                 400

Asp Leu Val Lys Tyr Phe Ile Ile Arg Asn Ser Cys Ser Asn Gln Arg
                405                 410                 415

Asp Ser Thr Ile His Val Glu Glu Asn Gly Gln Ser Ser Glu Ser Arg
            420                 425                 430

Phe Ser Val Gln Met Phe Met Phe Ala Gly His Tyr Asp Leu Val Phe
            435                 440                 445

Leu His Cys Glu Ile His Leu Cys Asp Ser Leu Asn Glu Gln Cys Gln
            450                 455                 460

Pro Ser Cys Ser Arg Ser Gln Val Arg Ser Glu Val Pro Ala Ile Asp
465                 470                 475                 480

Leu Ala Arg Val Leu Asp Leu Gly Pro Ile Thr Arg Arg Gly Ala Gln
                485                 490                 495

Ser Pro Gly Val Met Asn Gly Thr Pro Ser Thr Ala Gly Phe Leu Val
            500                 505                 510

Ala Trp Pro Met Val Leu Leu Thr Val Leu Leu Ala Trp Leu Phe
            515                 520                 525

<210> SEQ ID NO 2
<211> LENGTH: 537
<212> TYPE: PRT
<213> ORGANISM: Homo sapiens
<220> FEATURE:
<221> NAME/KEY: MISC_FEATURE
<223> OTHER INFORMATION: Glykoprotein 2

<400> SEQUENCE: 2

Met Pro His Leu Met Glu Arg Met Val Gly Ser Gly Leu Leu Trp Leu
1               5                   10                  15

Ala Leu Val Ser Cys Ile Leu Thr Gln Ala Ser Ala Val Gln Arg Gly
            20                  25                  30

Tyr Gly Asn Pro Ile Glu Ala Ser Ser Tyr Gly Leu Asp Leu Asp Cys
            35                  40                  45

Gly Ala Pro Gly Thr Pro Glu Ala His Val Cys Phe Asp Pro Cys Gln
        50                  55                  60

Asn Tyr Thr Leu Leu Asp Glu Pro Phe Arg Ser Thr Glu Asn Ser Ala
65                  70                  75                  80

Gly Ser Gln Gly Cys Asp Lys Asn Met Ser Gly Trp Tyr Arg Phe Val
                85                  90                  95

Gly Glu Gly Gly Val Arg Met Ser Glu Thr Cys Val Gln Val His Arg
            100                 105                 110

Cys Gln Thr Asp Ala Pro Met Trp Leu Asn Gly Thr His Pro Ala Leu

```
                115              120              125
    Gly Asp Gly Ile Thr Asn His Thr Ala Cys Ala His Trp Ser Gly Asn
    130              135              140
    Cys Cys Phe Trp Lys Thr Glu Val Leu Val Lys Ala Cys Pro Gly Gly
    145              150              155              160
    Tyr His Val Tyr Arg Leu Glu Gly Thr Pro Trp Cys Asn Leu Arg Tyr
                    165              170              175
    Cys Thr Val Pro Arg Asp Pro Ser Thr Val Glu Asp Lys Cys Glu Lys
                    180              185              190
    Ala Cys Arg Pro Glu Glu Cys Leu Ala Leu Asn Ser Thr Trp Gly
                195              200              205
    Cys Phe Cys Arg Gln Asp Leu Asn Ser Ser Asp Val His Ser Leu Gln
    210              215              220
    Pro Gln Leu Asp Cys Gly Pro Arg Glu Ile Lys Val Lys Val Asp Lys
    225              230              235              240
    Cys Leu Leu Gly Gly Leu Gly Leu Gly Glu Glu Val Ile Ala Tyr Leu
                    245              250              255
    Arg Asp Pro Asn Cys Ser Ser Ile Leu Gln Thr Glu Glu Arg Asn Trp
                    260              265              270
    Val Ser Val Thr Ser Pro Val Gln Ala Ser Ala Cys Arg Asn Ile Leu
                275              280              285
    Glu Arg Asn Gln Thr His Ala Ile Tyr Lys Asn Thr Leu Ser Leu Val
    290              295              300
    Asn Asp Phe Ile Ile Arg Asp Thr Ile Leu Asn Ile Asn Phe Gln Cys
    305              310              315              320
    Ala Tyr Pro Leu Asp Met Lys Val Ser Leu Gln Ala Ala Leu Gln Pro
                    325              330              335
    Ile Val Ser Ser Leu Asn Val Ser Val Asp Gly Asn Gly Glu Phe Ile
                    340              345              350
    Val Arg Met Ala Leu Phe Gln Asp Gln Asn Tyr Thr Asn Pro Tyr Glu
                355              360              365
    Gly Asp Ala Val Glu Leu Ser Val Glu Ser Val Leu Tyr Val Gly Ala
    370              375              380
    Ile Leu Glu Gln Gly Asp Thr Ser Arg Phe Asn Leu Val Leu Arg Asn
    385              390              395              400
    Cys Tyr Ala Thr Pro Thr Glu Asp Lys Ala Asp Leu Val Lys Tyr Phe
                    405              410              415
    Ile Ile Arg Asn Ser Cys Ser Asn Gln Arg Asp Ser Thr Ile His Val
                    420              425              430
    Glu Glu Asn Gly Gln Ser Ser Glu Ser Arg Phe Ser Val Gln Met Phe
                435              440              445
    Met Phe Ala Gly His Tyr Asp Leu Val Phe Leu His Cys Glu Ile His
    450              455              460
    Leu Cys Asp Ser Leu Asn Glu Gln Cys Gln Pro Ser Cys Ser Arg Ser
    465              470              475              480
    Gln Val Arg Ser Glu Val Pro Ala Ile Asp Leu Ala Arg Val Leu Asp
                    485              490              495
    Leu Gly Pro Ile Thr Arg Arg Gly Ala Gln Ser Pro Gly Val Met Asn
                    500              505              510
    Gly Thr Pro Ser Thr Ala Gly Phe Leu Val Ala Trp Pro Met Val Leu
                515              520              525
    Leu Thr Val Leu Leu Ala Trp Leu Phe
    530              535
```

```
<210> SEQ ID NO 3
<211> LENGTH: 534
<212> TYPE: PRT
<213> ORGANISM: Homo sapiens
<220> FEATURE:
<221> NAME/KEY: MISC_FEATURE
<223> OTHER INFORMATION: Glykoprotein 2

<400> SEQUENCE: 3
```

| Met | Pro | His | Leu | Met | Glu | Arg | Met | Val | Gly | Ser | Gly | Leu | Leu | Trp | Leu |
|---|---|---|---|---|---|---|---|---|---|---|---|---|---|---|---|
| 1 | | | | 5 | | | | | 10 | | | | | 15 | |

| Ala | Leu | Val | Ser | Cys | Ile | Leu | Thr | Gln | Ala | Ser | Ala | Val | Gln | Arg | Gly |
|---|---|---|---|---|---|---|---|---|---|---|---|---|---|---|---|
| | | | 20 | | | | | 25 | | | | | 30 | | |

| Tyr | Gly | Asn | Pro | Ile | Glu | Ala | Ser | Ser | Tyr | Gly | Leu | Asp | Leu | Asp | Cys |
|---|---|---|---|---|---|---|---|---|---|---|---|---|---|---|---|
| | | | 35 | | | | | 40 | | | | | 45 | | |

| Gly | Ala | Pro | Gly | Thr | Pro | Glu | Ala | His | Val | Cys | Phe | Asp | Pro | Cys | Gln |
|---|---|---|---|---|---|---|---|---|---|---|---|---|---|---|---|
| | 50 | | | | | 55 | | | | | 60 | | | | |

| Asn | Tyr | Thr | Leu | Leu | Asp | Glu | Pro | Phe | Arg | Ser | Thr | Glu | Asn | Ser | Ala |
|---|---|---|---|---|---|---|---|---|---|---|---|---|---|---|---|
| 65 | | | | | 70 | | | | | 75 | | | | | 80 |

| Gly | Ser | Gln | Gly | Cys | Asp | Lys | Asn | Met | Ser | Gly | Trp | Tyr | Arg | Phe | Val |
|---|---|---|---|---|---|---|---|---|---|---|---|---|---|---|---|
| | | | | 85 | | | | | 90 | | | | | 95 | |

| Gly | Glu | Gly | Gly | Val | Arg | Met | Ser | Glu | Thr | Cys | Val | Gln | Val | His | Arg |
|---|---|---|---|---|---|---|---|---|---|---|---|---|---|---|---|
| | | | 100 | | | | | 105 | | | | | 110 | | |

| Cys | Gln | Thr | Asp | Ala | Pro | Met | Trp | Leu | Asn | Gly | Thr | His | Pro | Ala | Leu |
|---|---|---|---|---|---|---|---|---|---|---|---|---|---|---|---|
| | | | 115 | | | | | 120 | | | | | 125 | | |

| Gly | Asp | Gly | Ile | Thr | Asn | His | Thr | Ala | Cys | Ala | His | Trp | Ser | Gly | Asn |
|---|---|---|---|---|---|---|---|---|---|---|---|---|---|---|---|
| | 130 | | | | | 135 | | | | | 140 | | | | |

| Cys | Cys | Phe | Trp | Lys | Thr | Glu | Val | Leu | Val | Lys | Ala | Cys | Pro | Gly | Gly |
|---|---|---|---|---|---|---|---|---|---|---|---|---|---|---|---|
| 145 | | | | | 150 | | | | | 155 | | | | | 160 |

| Tyr | His | Val | Tyr | Arg | Leu | Glu | Gly | Thr | Pro | Trp | Cys | Asn | Leu | Arg | Tyr |
|---|---|---|---|---|---|---|---|---|---|---|---|---|---|---|---|
| | | | | 165 | | | | | 170 | | | | | 175 | |

| Cys | Thr | Asp | Pro | Ser | Thr | Val | Glu | Asp | Lys | Cys | Glu | Lys | Ala | Cys | Arg |
|---|---|---|---|---|---|---|---|---|---|---|---|---|---|---|---|
| | | | 180 | | | | | 185 | | | | | 190 | | |

| Pro | Glu | Glu | Glu | Cys | Leu | Ala | Leu | Asn | Ser | Thr | Trp | Gly | Cys | Phe | Cys |
|---|---|---|---|---|---|---|---|---|---|---|---|---|---|---|---|
| | | | 195 | | | | | 200 | | | | | 205 | | |

| Arg | Gln | Asp | Leu | Asn | Ser | Ser | Asp | Val | His | Ser | Leu | Gln | Pro | Gln | Leu |
|---|---|---|---|---|---|---|---|---|---|---|---|---|---|---|---|
| | 210 | | | | | 215 | | | | | 220 | | | | |

| Asp | Cys | Gly | Pro | Arg | Glu | Ile | Lys | Val | Lys | Val | Asp | Lys | Cys | Leu | Leu |
|---|---|---|---|---|---|---|---|---|---|---|---|---|---|---|---|
| 225 | | | | | 230 | | | | | 235 | | | | | 240 |

| Gly | Gly | Leu | Gly | Leu | Gly | Glu | Glu | Val | Ile | Ala | Tyr | Leu | Arg | Asp | Pro |
|---|---|---|---|---|---|---|---|---|---|---|---|---|---|---|---|
| | | | | 245 | | | | | 250 | | | | | 255 | |

| Asn | Cys | Ser | Ser | Ile | Leu | Gln | Thr | Glu | Glu | Arg | Asn | Trp | Val | Ser | Val |
|---|---|---|---|---|---|---|---|---|---|---|---|---|---|---|---|
| | | | 260 | | | | | 265 | | | | | 270 | | |

| Thr | Ser | Pro | Val | Gln | Ala | Ser | Ala | Cys | Arg | Asn | Ile | Leu | Glu | Arg | Asn |
|---|---|---|---|---|---|---|---|---|---|---|---|---|---|---|---|
| | | 275 | | | | | 280 | | | | | 285 | | | |

| Gln | Thr | His | Ala | Ile | Tyr | Lys | Asn | Thr | Leu | Ser | Leu | Val | Asn | Asp | Phe |
|---|---|---|---|---|---|---|---|---|---|---|---|---|---|---|---|
| | 290 | | | | | 295 | | | | | 300 | | | | |

| Ile | Ile | Arg | Asp | Thr | Ile | Leu | Asn | Ile | Asn | Phe | Gln | Cys | Ala | Tyr | Pro |
|---|---|---|---|---|---|---|---|---|---|---|---|---|---|---|---|
| 305 | | | | | 310 | | | | | 315 | | | | | 320 |

| Leu | Asp | Met | Lys | Val | Ser | Leu | Gln | Ala | Ala | Leu | Gln | Pro | Ile | Val | Ser |
|---|---|---|---|---|---|---|---|---|---|---|---|---|---|---|---|
| | | | | 325 | | | | | 330 | | | | | 335 | |

| Ser | Leu | Asn | Val | Ser | Val | Asp | Gly | Asn | Gly | Glu | Phe | Ile | Val | Arg | Met |
|---|---|---|---|---|---|---|---|---|---|---|---|---|---|---|---|
| | | | 340 | | | | | 345 | | | | | 350 | | |

| Ala | Leu | Phe | Gln | Asp | Gln | Asn | Tyr | Thr | Asn | Pro | Tyr | Glu | Gly | Asp | Ala |
|---|---|---|---|---|---|---|---|---|---|---|---|---|---|---|---|
| | | 355 | | | | | 360 | | | | | 365 | | | |

```
Val Glu Leu Ser Val Glu Ser Val Leu Tyr Val Gly Ala Ile Leu Glu
    370                 375                 380

Gln Gly Asp Thr Ser Arg Phe Asn Leu Val Leu Arg Asn Cys Tyr Ala
385                 390                 395                 400

Thr Pro Thr Glu Asp Lys Ala Asp Leu Val Lys Tyr Phe Ile Ile Arg
                405                 410                 415

Asn Ser Cys Ser Asn Gln Arg Asp Ser Thr Ile His Val Glu Glu Asn
                420                 425                 430

Gly Gln Ser Ser Glu Ser Arg Phe Ser Val Gln Met Phe Met Phe Ala
                435                 440                 445

Gly His Tyr Asp Leu Val Phe Leu His Cys Glu Ile His Leu Cys Asp
    450                 455                 460

Ser Leu Asn Glu Gln Cys Gln Pro Ser Cys Ser Arg Ser Gln Val Arg
465                 470                 475                 480

Ser Glu Val Pro Ala Ile Asp Leu Ala Arg Val Leu Asp Leu Gly Pro
                485                 490                 495

Ile Thr Arg Arg Gly Ala Gln Ser Pro Gly Val Met Asn Gly Thr Pro
                500                 505                 510

Ser Thr Ala Gly Phe Leu Val Ala Trp Pro Met Val Leu Leu Thr Val
                515                 520                 525

Leu Leu Ala Trp Leu Phe
    530

<210> SEQ ID NO 4
<211> LENGTH: 390
<212> TYPE: PRT
<213> ORGANISM: Homo sapiens
<220> FEATURE:
<221> NAME/KEY: MISC_FEATURE
<223> OTHER INFORMATION: Glykoprotein 2

<400> SEQUENCE: 4

Met Pro His Leu Met Glu Arg Met Val Gly Ser Gly Leu Leu Trp Leu
1               5                   10                  15

Ala Leu Val Ser Cys Ile Leu Thr Gln Ala Ser Ala Val Gln Arg Val
                20                  25                  30

Pro Arg Asp Pro Ser Thr Val Glu Asp Lys Cys Glu Lys Ala Cys Arg
                35                  40                  45

Pro Glu Glu Glu Cys Leu Ala Leu Asn Ser Thr Trp Gly Cys Phe Cys
                50                  55                  60

Arg Gln Asp Leu Asn Ser Ser Asp Val His Ser Leu Gln Pro Gln Leu
65                  70                  75                  80

Asp Cys Gly Pro Arg Glu Ile Lys Val Lys Val Asp Lys Cys Leu Leu
                85                  90                  95

Gly Gly Leu Gly Leu Gly Glu Glu Val Ile Ala Tyr Leu Arg Asp Pro
                100                 105                 110

Asn Cys Ser Ser Ile Leu Gln Thr Glu Glu Arg Asn Trp Val Ser Val
                115                 120                 125

Thr Ser Pro Val Gln Ala Ser Ala Cys Arg Asn Ile Leu Glu Arg Asn
                130                 135                 140

Gln Thr His Ala Ile Tyr Lys Asn Thr Leu Ser Leu Val Asn Asp Phe
145                 150                 155                 160

Ile Ile Arg Asp Thr Ile Leu Asn Ile Asn Phe Gln Cys Ala Tyr Pro
                165                 170                 175

Leu Asp Met Lys Val Ser Leu Gln Ala Ala Leu Gln Pro Ile Val Ser
                180                 185                 190
```

```
Ser Leu Asn Val Ser Val Asp Gly Asn Gly Glu Phe Ile Val Arg Met
    195                 200                 205

Ala Leu Phe Gln Asp Gln Asn Tyr Thr Asn Pro Tyr Glu Gly Asp Ala
    210                 215                 220

Val Glu Leu Ser Val Glu Ser Val Leu Tyr Val Gly Ala Ile Leu Glu
225                 230                 235                 240

Gln Gly Asp Thr Ser Arg Phe Asn Leu Val Leu Arg Asn Cys Tyr Ala
                245                 250                 255

Thr Pro Thr Glu Asp Lys Ala Asp Leu Val Lys Tyr Phe Ile Ile Arg
                260                 265                 270

Asn Ser Cys Ser Asn Gln Arg Asp Ser Thr Ile His Val Glu Glu Asn
275                 280                 285

Gly Gln Ser Ser Glu Ser Arg Phe Ser Val Gln Met Phe Met Phe Ala
    290                 295                 300

Gly His Tyr Asp Leu Val Phe Leu His Cys Glu Ile His Leu Cys Asp
305                 310                 315                 320

Ser Leu Asn Glu Gln Cys Gln Pro Ser Cys Ser Arg Ser Gln Val Arg
                325                 330                 335

Ser Glu Val Pro Ala Ile Asp Leu Ala Arg Val Leu Asp Leu Gly Pro
                340                 345                 350

Ile Thr Arg Arg Gly Ala Gln Ser Pro Gly Val Met Asn Gly Thr Pro
                355                 360                 365

Ser Thr Ala Gly Phe Leu Val Ala Trp Pro Met Val Leu Leu Thr Val
370                 375                 380

Leu Leu Ala Trp Leu Phe
385                 390

<210> SEQ ID NO 5
<211> LENGTH: 387
<212> TYPE: PRT
<213> ORGANISM: Homo sapiens
<220> FEATURE:
<221> NAME/KEY: MISC_FEATURE
<223> OTHER INFORMATION: Glykoprotein 2

<400> SEQUENCE: 5

Met Pro His Leu Met Glu Arg Met Val Gly Ser Gly Leu Leu Trp Leu
1               5                   10                  15

Ala Leu Val Ser Cys Ile Leu Thr Gln Ala Ser Ala Val Gln Arg Asp
                20                  25                  30

Pro Ser Thr Val Glu Asp Lys Cys Glu Lys Ala Cys Arg Pro Glu Glu
            35                  40                  45

Glu Cys Leu Ala Leu Asn Ser Thr Trp Gly Cys Phe Cys Arg Gln Asp
    50                  55                  60

Leu Asn Ser Ser Asp Val His Ser Leu Gln Pro Gln Leu Asp Cys Gly
65                  70                  75                  80

Pro Arg Glu Ile Lys Val Lys Val Asp Lys Cys Leu Leu Gly Gly Leu
                85                  90                  95

Gly Leu Gly Glu Glu Val Ile Ala Tyr Leu Arg Asp Pro Asn Cys Ser
            100                 105                 110

Ser Ile Leu Gln Thr Glu Glu Arg Asn Trp Val Ser Val Thr Ser Pro
    115                 120                 125

Val Gln Ala Ser Ala Cys Arg Asn Ile Leu Glu Arg Asn Gln Thr His
    130                 135                 140

Ala Ile Tyr Lys Asn Thr Leu Ser Leu Val Asn Asp Phe Ile Ile Arg
145                 150                 155                 160
```

-continued

```
Asp Thr Ile Leu Asn Ile Asn Phe Gln Cys Ala Tyr Pro Leu Asp Met
            165                 170                 175
Lys Val Ser Leu Gln Ala Ala Leu Gln Pro Ile Val Ser Ser Leu Asn
            180                 185                 190
Val Ser Val Asp Gly Asn Gly Glu Phe Ile Val Arg Met Ala Leu Phe
            195                 200                 205
Gln Asp Gln Asn Tyr Thr Asn Pro Tyr Glu Gly Asp Ala Val Glu Leu
            210                 215                 220
Ser Val Glu Ser Val Leu Tyr Val Gly Ala Ile Leu Glu Gln Gly Asp
225                 230                 235                 240
Thr Ser Arg Phe Asn Leu Val Leu Arg Asn Cys Tyr Ala Thr Pro Thr
            245                 250                 255
Glu Asp Lys Ala Asp Leu Val Lys Tyr Phe Ile Ile Arg Asn Ser Cys
            260                 265                 270
Ser Asn Gln Arg Asp Ser Thr Ile His Val Glu Glu Asn Gly Gln Ser
            275                 280                 285
Ser Glu Ser Arg Phe Ser Val Gln Met Phe Met Phe Ala Gly His Tyr
            290                 295                 300
Asp Leu Val Phe Leu His Cys Glu Ile His Leu Cys Asp Ser Leu Asn
305                 310                 315                 320
Glu Gln Cys Gln Pro Ser Cys Ser Arg Ser Gln Val Arg Ser Glu Val
            325                 330                 335
Pro Ala Ile Asp Leu Ala Arg Val Leu Asp Leu Gly Pro Ile Thr Arg
            340                 345                 350
Arg Gly Ala Gln Ser Pro Gly Val Met Asn Gly Thr Pro Ser Thr Ala
            355                 360                 365
Gly Phe Leu Val Ala Trp Pro Met Val Leu Leu Thr Val Leu Leu Ala
            370                 375                 380
Trp Leu Phe
385
```